(12) United States Patent
Do

(10) Patent No.: US 8,263,055 B2
(45) Date of Patent: Sep. 11, 2012

(54) LONG LASTING AND WATERPROOF LASH EXTENSION COMPOSITION

(75) Inventor: Thi N. Do, West Orange, NJ (US)

(73) Assignee: Avon Products, Inc., New York, NY (US)

( * ) Notice: Subject to any disclaimer, the term of this patent is extended or adjusted under 35 U.S.C. 154(b) by 1396 days.

(21) Appl. No.: 11/832,217

(22) Filed: Aug. 1, 2007

(65) Prior Publication Data

US 2009/0035246 A1 Feb. 5, 2009

(51) Int. Cl.
*A61Q 1/10* (2006.01)
(52) U.S. Cl. ...................................... 424/70.7
(58) Field of Classification Search .................. None
See application file for complete search history.

(56) References Cited

U.S. PATENT DOCUMENTS

| | | | |
|---|---|---|---|
| 3,159,601 A | 12/1964 | Ashby | |
| 3,159,662 A | 12/1964 | Ashby | |
| 3,220,972 A | 11/1965 | Lamoreaux | |
| 3,254,111 A | 5/1966 | Hawkins et al. | |
| 3,445,420 A | 5/1969 | Kookootsedes et al. | |
| 3,576,027 A | 4/1971 | Gaylord | |
| 3,591,676 A | 7/1971 | Hawkins et al. | |
| 3,715,334 A | 2/1973 | Karstedt | |
| 3,775,452 A | 11/1973 | Karstedt | |
| 3,814,730 A | 6/1974 | Karstedt | |
| 4,104,333 A | 8/1978 | Lee, Jr. et al. | |
| 4,256,870 A | 3/1981 | Eckberg | |
| 4,465,818 A | 8/1984 | Shirahata et al. | |
| 4,562,096 A | 12/1985 | Lo et al. | |
| 4,650,826 A | 3/1987 | Waniczek et al. | |
| 4,681,963 A | 7/1987 | Lewis | |
| 4,892,907 A | 1/1990 | Lampe et al. | |
| 5,118,755 A | 6/1992 | Endo et al. | |
| 5,328,966 A | 7/1994 | Nagaoka | |
| 5,340,899 A | 8/1994 | Altes | |
| 5,556,914 A | 9/1996 | Colas et al. | |
| 5,610,259 A | 3/1997 | Cella et al. | |
| 5,629,387 A | 5/1997 | Frances et al. | |
| 5,789,334 A | 8/1998 | Nakanishi et al. | |
| 5,889,108 A * | 3/1999 | Zhang | 524/862 |
| 5,969,057 A | 10/1999 | Schoeley et al. | |
| 6,191,202 B1 | 2/2001 | Greff et al. | |
| 6,235,832 B1 | 5/2001 | Deng et al. | |
| 6,277,358 B1 * | 8/2001 | Calello et al. | 424/61 |
| 6,303,728 B1 | 10/2001 | Hagimori et al. | |
| 6,307,082 B1 | 10/2001 | Klein et al. | |
| 6,323,275 B2 | 11/2001 | Takahashi et al. | |
| 6,471,985 B2 | 10/2002 | Guyuron et al. | |
| 6,656,487 B2 | 12/2003 | Afriat et al. | |
| 6,726,917 B2 | 4/2004 | Kanji et al. | |
| 6,833,407 B1 | 12/2004 | Ahmed et al. | |
| 6,896,877 B2 | 5/2005 | Calello et al. | |
| 6,989,421 B2 | 1/2006 | Grady | |
| 6,995,227 B2 | 2/2006 | Ryan et al. | |
| 7,049,384 B1 | 5/2006 | Friebe et al. | |
| 7,119,159 B2 | 10/2006 | Fehn et al. | |
| 7,750,106 B2 * | 7/2010 | Zheng et al. | 528/34 |
| 8,034,323 B2 * | 10/2011 | Zheng et al. | 424/64 |
| 2002/0168335 A1 | 11/2002 | Collin | |
| 2004/0147670 A1 * | 7/2004 | Hupfield | 524/588 |
| 2005/0000531 A1 | 1/2005 | Shi | |
| 2005/0061349 A1 | 3/2005 | Patel et al. | |
| 2005/0112072 A1 * | 5/2005 | Wang et al. | 424/63 |
| 2007/0142575 A1 | 6/2007 | Zheng et al. | |
| 2007/0142599 A1 | 6/2007 | Zheng et al. | |

FOREIGN PATENT DOCUMENTS

| | | | |
|---|---|---|---|
| EP | 1101487 | * | 5/2001 |
| EP | 1400234 | * | 3/2004 |
| EP | 1426027 | * | 6/2004 |
| EP | 1516612 A2 | | 3/2005 |
| WO | WO9515741 A1 | | 6/1995 |
| WO | WO 2007/071706 | * | 6/2007 |
| WO | WO 2007/071885 | * | 6/2007 |

* cited by examiner

Primary Examiner — Jyothsna Venkat
(74) Attorney, Agent, or Firm — Joan M. McGillycuddy; Charles J. Zeller; David M. Joyal

(57) ABSTRACT

Compositions and methods for the in situ formation of cross-linked polymeric filaments are disclosed. The disclosed filaments are preferably elastomeric, water-resistant, oil-resistant, long-wearing. The filament forming compositions generally comprise one or more cross-linkable polymers having at least one functional group capable of forming cross-links and a cross-linking agent, the presence of which promotes cross-linking of the polymers. The compositions may be used for lengthening and/or volumizing keratin fibers, for example, eyelashes.

6 Claims, 1 Drawing Sheet

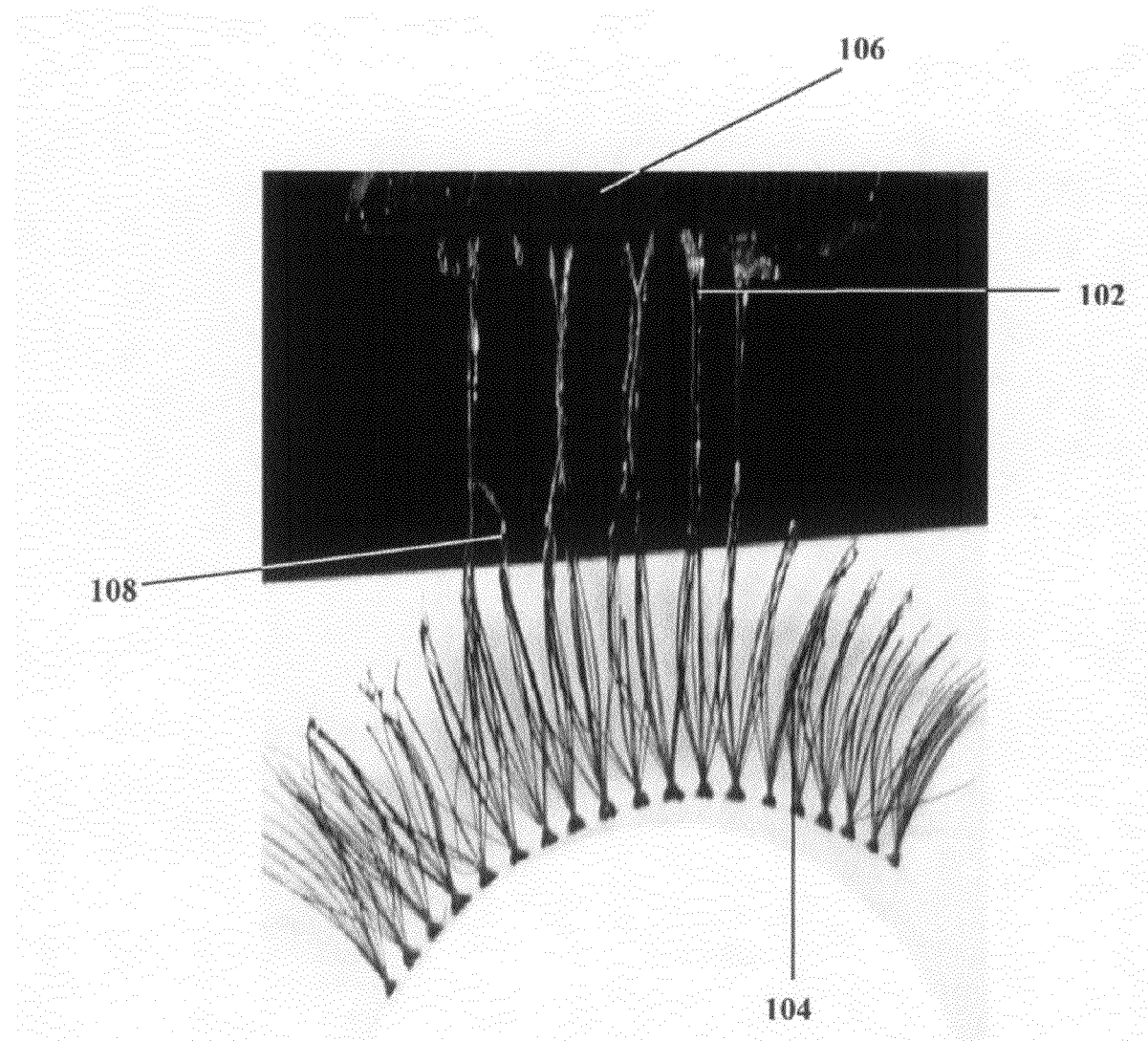

LONG LASTING AND WATERPROOF LASH EXTENSION COMPOSITION

FIELD OF INVENTION

The present invention relates generally to compositions and methods for forming filaments on a biological surface. More particularly, the invention relates to polymeric filaments formed on keratin fibers, such as, eyelashes, eyebrows and/or hairs of the scalp, thereby volumizing and/or lengthening the appearance of the keratin fibers.

BACKGROUND OF THE INVENTION

A number of cosmetic and personal care compositions have been utilized, particularly by women, to enhance and/or emphasize the appearance of keratin fibers, such as eyelashes. Such enhancements may include the impartation of color (or tone), volume (i.e., thickness), length and curl. Pre-formed fibers have been added to a number of mascara formulations for the purpose of enhancing the volume and/or length of eyelashes. Examples of mascara formulations containing pre-formed fibers are described in U.S. Pat. No. 6,726,917 ("the '917 patent") and U.S. Pat. No. 6,656,487 ("the '487 patent"). The '917 patent provides a volumizing and/or lengthening mascara composition having pre-formed fibers, pigments, a water-soluble film former and an oil-soluble film former. The '487 patent describes a composition having pre-formed fibers and a copolymer having carboxylate groups and polydimethylsiloxane groups. The size of pre-formed fibers that can be incorporated into a mascara composition is limited by the viscosity and consistency of the overall mascara composition. In addition, mascara formulations having pre-formed fibers may form aggregates, which is visually unappealing and undesirable for a cosmetic formulation. Furthermore, pre-formed fibers contained within mascara formulations can often break from the eyelashes and fall into the eye, causing irritation, particularly for users with sensitive eyes or those who that wear contact lenses. In view of these practical considerations, pre-formed fibers incorporated into a mascara composition must be limited in length and thereby restricting the lengthening and/or volumizing benefits of adding pre-formed fibers to a mascara formulation.

There are a number of other methods for lengthening and/or volumizing eyelashes. One method for increasing appeared length and/or volume of eyelashes is by applying false eyelashes. False eyelashes are physical filamentous extensions applied onto an edge of an eyelid. Typically, false eyelashes include a base structure having pre-formed filaments extending therefrom. The base structure may be applied onto an eyelid with an adhesive. Application of false eyelashes is often difficult and cumbersome and may require the assistance of a professional makeup artist.

An alternative method used in the art for lengthening and/or volumizing eyelashes includes multiple applications of at least one cosmetic composition, where each application incrementally lengthens and/or volumizes the eyelashes. This lengthening and volumizing effect may be achieved by (1) multiple applications of a single composition or (2) multiple sequential applications of two or more different compositions.

In the first technique, a mascara formulation having a single composition is applied as a first layer to lengthen and volumize the eyelashes and left to set or dry. Subsequently, a second layer of the single composition is applied over the first layer. The second layer incrementally lengthens and/or volumizes the eyelashes in addition to that of the first layer. Application of the single composition may be repeated as many times as needed to yield the desired length and/or volume. Typically, these single compositions are wax-based and/or polymer-based, for example, PCT Application Publication No. WO 95/15741 and U.S. Patent Application Publication No. 2002/0168335, both of which disclose cosmetic compositions having wax and polymer.

In the second technique, a mascara formulation having two different compositions are applied alternately. A first composition, which is generally clear or white in color, is applied to eyelashes to lengthen and/or volumize the eyelashes and is allowed to set or dry. Once the first composition has set, a second composition, which is typically of a color such as black, brown, or blue, is applied over the first composition to further lengthen and/or volumize the eyelashes. Application of the first composition followed by the second composition may be repeated to incrementally lengthen and/or volumize eyelashes until a desired length or volume is reached. Examples of cosmetic formulations of the second technique include methods for applying a two-step mascara formulation by applying a washable mascara composition followed by applying a waterproof mascara composition, wherein the washable mascara composition, the waterproof mascara composition, or both may contain pre-formed fibers, such as, European Patent Application Publication No. 1516612 and U.S. Patent Application Publication No. 2005/0061349.

The aforementioned multiple-application techniques for lengthening and/or volumizing eyelashes are time-consuming and tedious because each layer provides only an incremental and gradual increase in length and/or volume. Between applying each additional layer, a user must wait for the previous layer to dry or set before applying a subsequent layer. Therefore, to noticeably enhance and/or emphasize the eyelashes, the user must apply multiple layers of the cosmetic formulation and wait for a period of time following each application to achieve the desired length and/or volume.

Liquid compositions comprising cross-linkable polymers are known in the industrial coating industry. These compositions may also include some type of cross-linkable chemical moiety within the structure of the cross-linkable polymer, as well as other ingredients such as solvents, dispersants, coalescents, and the like. These cross-linkable polymers are typically polymeric film formers and have been used in products such as paints, varnishes, lacquers, and the like. They are known to provide tough and resilient coatings.

Some cross-linkable compositions of this type are two-part, two-container systems, wherein a first part comprises the a first film forming polymer and a second part comprises a second film forming polymer cross-linkable with the first film forming polymer, and wherein the first part is physically separated from the second part just prior to use. Upon mixing the first part with the second part, such compositions then immediately react to form the cross-linked film coating. Alternatively, other systems are two-part, one-container systems, wherein the film forming polymer and the cross-linking agent are present in the same container. Blocking agents are typically included in two-part, one-container systems. The blocking agents inhibit the film forming polymers from cross-linking prior to use. The blocking agents are generally volatile agents. After a composition is applied to a desired substrate, a blocking agent therein evaporates and permits cross-linking of the film forming polymers.

Cross-linkable monomeric coatings have been used in the manufacture of artificial nail coatings, also known as "wraps" or "tips" to produce permanent coatings. For example, U.S. Pat. No. 4,104,333 teaches self-curing artificial fingernail compositions having cross-linking monomers. Upon application of the composition to a natural nail of a finger or toe, the monomers cross-link and form in situ a permanent, thick, artificial coating on top of the natural nail. If a lengthened artificial nail is desired, an extender is affixed to the end of the natural nail and the monomer composition is applied over the natural nail and extender and allowed to set or polymerize.

There is a continuing need in the art for cosmetic and personal care product, particularly mascara formulations, that overcome one or more of the foregoing deficiencies of conventional cosmetic products for lengthening or volumizing keratin fibers. It would be desirable to provide a cosmetic formulation and a method for lengthening or volumizing keratin fibers that is fast and effective without the cumbersome application of false eyelashes or tediously compounding incremental and gradual increases using a multiple-application technique. It would also be desirable to avoid the use of pre-formed fibers, which as discussed above, may break and cause eye irritation, and apply the in-situ polymerization technique from artificial nail coatings to keratin fiber lengthening and/or volumizing cosmetic formulations.

It is an object of the invention to provide a method for lengthening or volumizing keratin fibers, including eyelashes, eyebrows and hairs of the scalp.

It is further an object of the invention to provide a long-lasting cosmetic formulation for lengthening or volumizing keratin fibers, wherein the cosmetic formulation remains on the keratin fibers for an extended period of time.

SUMMARY OF INVENTION

In accordance with the foregoing objectives and others, the present invention overcomes the deficiencies associated with the prior art by providing in situ filament forming compositions for use in cosmetics which are flexible yet durable and provide for a heretofore unobtainable fast and effective way for lengthening and/or volumizing keratin fibers.

In one aspect of the invention, a method for forming a filament on a keratin fiber is provided. Generally, the method comprises applying to the keratin fiber one or more cross-linkable polymers having at least one functional group and a cross-linking agent. The cross-linkable polymers are capable of forming cross-links in situ in the presence of the cross-linking agent, which promotes cross-linking of the cross-linkable polymers through reaction of the functional groups. The method also comprises drawing out a portion of the polymers beyond a terminal end of the keratin fiber while the polymer is in a fluid or partially fluid state. The cross-linkable polymers are then permitted to cure to a solid, thereby forming a filamentous extension on the keratin fiber. The compositions and methods of the invention do not require repeated application of a composition to incrementally form a lash extension nor are pre-formed polymeric filaments required to achieve the volumizing and/or lengthening effect.

BRIEF DESCRIPTION OF THE DRAWINGS

FIG. 1 shows an exemplary embodiment of a method for lengthening and/or volumizing keratin fibers according to the present invention.

DETAILED DESCRIPTION

As used herein, all terms are intended to have their ordinary and accustomed meaning in the art unless otherwise explicitly defined. As used herein, the term "keratin fibers" may include, without limitation, eyelashes, eyebrows, or hair. The term "polymer" is intended to embrace homopolymers, copolymers and the like and includes oligomers. The term "monomer" may include monomers, oligomers and polymers which themselves constitute units for further polymerization.

The present invention is founded on the surprising discovery that cosmetic formulations comprising reagents for forming certain cross-linked polymers are capable of providing long-wearing cosmetic filaments on biological surfaces, particularly on keratin fibers. The filaments are formed in situ on the keratin fibers upon application thereto, meaning that the cross-linking reaction occurs on the keratin fibers after application of the cosmetic formulation. Depending on the selection of cross-linkable polymers, the resulting filament may range from hard to flexible. The cosmetic formulations of the invention are preferably applied to keratin fibers, particularly eyelashes, to lengthen and/or volumize the keratin fibers.

A. Filament Forming Components

One component of the invention is one or more cross-linkable polymers having at least one functional group capable of forming cross-links. The composition should preferably cure (i.e., form cross-links) in situ, meaning that the composition is fluid or spreadable prior to application, to enable it to be easily applied to the lashes and form a continuous coat thereon, and subsequently become increasingly viscous as the lashes are brushed, and ultimately harden into a solid filament. The film forming components are typically selected such that the polymer cures to a hardened filament within 5 minutes of application to the lashes, preferably within 2 minutes, and more preferably within one minute, with brushing to facilitate mixing of the components.

The polymers may be hydrophilic, hydrophobic, or any combination thereof depending on the desired properties of the cosmetic formulation. In the broadest sense of the invention, the selection of the cross-linkable polymers are not particularly limited and will embrace any polymer comprising reactive functional groups which are capable of forming cross-links. Typically, though not necessarily, the cross-linking polymers will include at least one elastomer. Preferably, the polymers include a silicone polymer, such as a diorganosiloxane polymer.

The cosmetic formulation of the present invention will typically include a polymer known to be useful in the art as a self-adhesive, thermosetting, sealant, release coating or the like. The polymer may comprise, for example, epoxy, acrylate, urethane, and/or siloxane units, to name a few. Preferably, the cross-linkable polymers are safe for cosmetic applications, including those known in the art as cosmetic film forming polymers. Ideally, the cross-linkable polymers may include any polymer known in the art to be safe for applications to keratin fibers, and particularly those known in the art to be safe for application near the eyes, such as eyelashes.

The cross-linkable polymers cross-link to form higher molecular weight polymers through reaction of the at least one functional group. The cosmetic formulation of the present invention may optionally include one or more cross-linking agent (e.g., reactive monomers, catalysts, or initiators) to promote reaction of the functional group(s). Preferably, the cross-linking reaction forms a polymeric network, which is believed to impart improved tensile strength to the cosmetic formulation. The reaction may be, for example, an addition polymerization reaction (also known as chain-growth polymerization) or a condensation polymerization reaction (also known as step-growth polymerization).

The filament forming composition may include, for example, a film-forming polymer conventionally employed in the cosmetic arts which has been functionalized with groups capable of cross-linking upon exposure to a cross-linking agent. The cross-linking agent may be for, example, a monomer which is reactive with the functional groups on the film-forming polymer. Alternatively, the cross-linking agent may be a catalyst, initiator, activator or the like which promotes cross-inking of the film forming polymer in the case where the polymer comprises two different functional groups which are reactive with each other in the presence of the cross-linking agent. Suitable functionalized film-forming polymers which can be cross-linked in situ are described in, without limitation, U.S. Pat. No. 6,896,877 to Calello et al., the disclosure of which is hereby incorporated by reference. The film-forming polymer can contain, for example, reactive hydroxyl, carboxyl, isocyanate, halogen, alkylene, acetoacetoxy, epoxy, and/or amino groups.

Film-forming polymers functionalized with reactive carboxyl groups can be prepared, for example, from homopolymers or copolymers derived from free radical polymerization of acrylic acid, methacrylic acid and the like. Mention is made of polymers which include the reaction product of a monomer mixture of one or more non-functional methacrylate monomers with one or more functional acrylate monomers having reactive functional groups. The reaction product preferably includes a low polydispersity, low molecular weight copolymer having an average of 2 to 25 reactive functional groups. The functional groups, include without limitation hydroxyl, acetoacetoxy, carboxyl, epoxy, primary and secondary amine, and a combination thereof. Polymers of hydroxyalkyl acrylates and hydroxyalkyl methacrylates are one example of acrylate polymers which are capable of in situ cross-linking in the presence of a cross-linking agent.

Polymers such as polyesters, polyamides, and polyimides which are the condensation products of diacids, diesters, diamines, diols and the like, as known to those skilled in the art, are also contemplated to be suitable cross-linkable polymers when functionalized with one or more reactive functional groups (e.g., epoxy). Polymers such as polyurethanes, polyimidazoles, and cured epoxy resins, such as those formed from addition polymerization of monomers such as diisocyanates, diols, diamines, and dialdehydes, or epoxy resins (e.g., epichlorohydrin and bisphenol-A) are also contemplated to be suitable for in situ cross-linking in the presence of a suitable cross-linking agent.

The cyanoacrylate class of adhesives is also contemplated to be useful in the practice of the invention. Cyanoacrylates are capable of hardening in situ by an anionic polymerization reaction of ester of 2-cyanoacrylic acid. Suitable esters include, without limitation, alkyl, alkenyl, cycloalkyl, aryl, alkoxyalkyl, aralkyl or haloalkyl or the like. Particular mention is made of the methyl, ethyl, n-propyl, isopropyl, n-butyl, isobutyl, pentyl, hexyl, allyl, methallyl, crotyl, propargyl, cyclohexyl, benzyl, phenyl, cresyl, 2-chloroethyl, 3-chloropropyl, 2-chlorobutyl, trifluoroethyl, 2-methoxyethyl, 3-methoxybutyl or 2-ethoxyethyl esters, with preference given to the allyl, methoxyethyl, ethoxyethyl, methyl, ethyl, propyl, isopropyl or butyl esters of 2-cyanoacrylic acid. Polymers comprising combinations of two or more of the foregoing 2-cyanoacrylic acid esters are also contemplated to be useful. Various cyanoacrylate adhesives systems are described in, for example, U.S. Pat. No. 6,995,227 to Ryan, et al.; U.S. Pat. No. 6,191,202 to Greff, et al.; U.S. Pat. No. 6,323,275 to Takahashi, et al.; U.S. Pat. No. 4,650,826 to Waniczek, et al. U.S. Pat. No. 3,591,676 to Hawkins et al.; U.S. Pat. No. 3,254,111 to Hawkins et al., the disclosures of which are hereby incorporated by reference. Suitable cyanolacrylate adhesives include the methyl, ethyl, modified ethyl, and alkoxy-ethyl cyanoacrylates commercially available under the tradename PARFIX™ from Parsons Adhesives, Inc. (Rochester, Mich.).

In the currently preferred practice of the invention, the cross-linkable polymer is a silicon polymer, such as a polydimethylsiloxane (PDMS) polymer. Suitable cross-linking silicon polymer compositions are well-known in the art and disclosed in, for example, U.S. Pat. No. 7,119,159 to Fehn, et al.; U.S. Pat. No. 7,049,384 to Friebe, et al.; U.S. Pat. No. 6,989,421 to Grady; U.S. Pat. No. 6,896,877 to Calello, et al.; U.S. Pat. No. 6,833,407 to Ahmed, et al.; U.S. Pat. No. 6,471,985 to Guyuron, et al.; U.S. Pat. No. 6,235,832 to Deng, et al.; U.S. Pat. No. 5,969,057 to Schoeley, et al.; U.S. Pat. No. 5,610,259 to Cella, et al.; U.S. Pat. No. 5,556,914 to Colas, et al.; U.S. Pat. No. 5,340,899 to Altes; U.S. Pat. No. 5,328,966 to Nagaoka; U.S. Pat. No. 5,118,755 to Endo, et al.; and U.S. Pat. No. 4,892,907 to Lampe, et al., the disclosures of which are hereby incorporated by reference in their entirety.

The siloxane polymer may undergo cross-linking by any method known in the art, including without limitation, in situ cross-linking by hydrosilylation reaction or by polycondensation reaction as discussed in detail below.

i. Filament Forming Components Having In-Situ Hydrosilylation Cross-Linking

In one embodiment, the cross-linkable polymers may comprise:

(1) a siloxane polymer comprising at least two side chains or terminal groups comprising an alkenyl functional group, and (2) a hydrosilane polymer having at least two reactive Si—H bonds at either the terminal ends of the polymer or on one or more side chains.

In the presence of hydrosilane, the alkenyl-functionalized siloxane polymer undergoes metal catalyzed in situ cross-linking through an addition reaction of hydrosilane with the olefinic moieties. The addition reaction is illustrated below in the non-limiting case of a divinyl-terminated polydimethylsiloxane and a dihydrido-terminated polydimethylsiloxane:

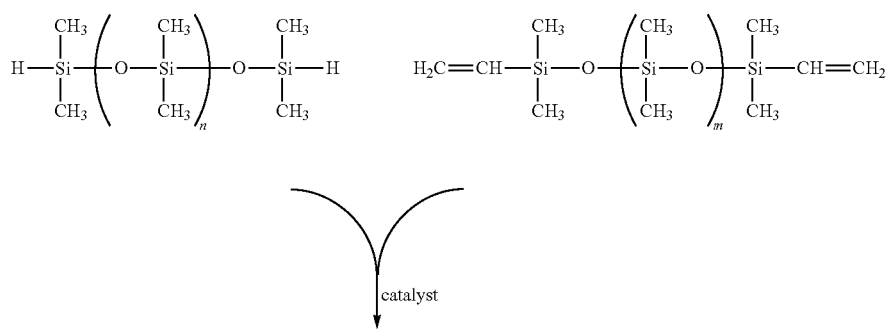

-continued

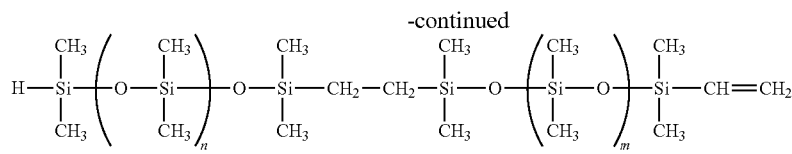

As illustrated above, the addition reaction results in the formation of a Si—C bonds between the hydrosilane and the alkenyl-functionalized siloxane polymer. Because each of the polymers are di-functional, the cross-linking proceeds through further reaction at the hydrosilyl or alkenyl reactive ends of the resultant polymer to create higher order structures.

A necessary component of this preferred embodiment is alkenyl-functionalized organopolysiloxane. There is essentially no constraint on the selection of a suitable alkenyl-functionalized organopolysiloxane. In certain preferred embodiments, the polymer will comprise at least two alkenyl-functionalized sites which may be at the terminal end of the polymer or on a side chain. The alkenyl functionality is preferably a mono-substituted olefin such as vinyl, 1-propenyl, 1-butenyl, and the like, but may, alternatively by a di-, tri-, or tetra-substituted olefin.

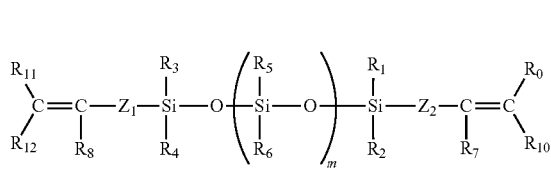

I

Typically, but not necessarily, the alkenyl-functionalized organopolysiloxanes will have the structure shown in formula I:

wherein $R_1$, $R_2$, $R_3$, $R_4$, $R_5$, and $R_6$ are independently selected at each occurrence from substituted or unsubstituted branched or straight chain $C_1$-$C_{10}$ alkyl, alkenyl, or alkynyl group, including without limitation methyl, ethyl, propyl, isopropyl, butyl, isobutyl, t-butyl, pentyl, hexyl, vinyl, allyl, butenyl, pentenyl, hexenyl, propynyl, butynyl, n-pentyl, iso-pentyl, neo-pentyl, tert-pentyl; cycloalkyl, heterocycloalkyl, haloalkyl, benzyl, alkyl-aryl; substituted or unsubstituted aryl or heteroaryl groups; $C_1$-$C_6$ alkoxy, amino, alkyl amino, dialkyl amino, hydroxyl, hydrogen, carboxy, cyano, or halogen; or $R_1$, $R_2$, $R_3$, $R_4$, $R_5$, and $R_6$ may each independently represent branching points in the organopolysiloxane backbone whereby D, T, or Q structures are introduced. Preferably $R_4$ is methyl.

In one embodiment, $R_5$, and $R_6$ are both methyl such that the polymer comprises the repeat unit of a polydimethylsiloxane (PDMS) polymer. In another embodiment, $R_1$, $R_2$, $R_3$, and $R_4$ are each methyl. In a preferred embodiment, $R_1$, $R_2$, $R_3$, $R_4$, $R_5$, and $R_6$ are each methyl.

$Z_1$ and $Z_2$ may each represent a bond between Si and the adjacent olefinic carbon atom or $Z_1$ and $Z_2$ may each be a linker moiety independently selected from O; S; $NR^a$ where "$R^a$" represents an alkyl, alkynyl, alkynyl, aryl, heteroaryl, or alkyl-aryl group; substituted or unsubstituted branched or straight chain $C_1$-$C_{10}$ alkyl, alkenyl, alkynyl, aryl, heteroaryl, or alkyl-aryl groups, including without limitation, linear alkyl moieties of the form —$(CH_2)_a$— where "a" is an integer from 1 to 10, including, for example, —$CH_2$—, —$CH_2CH_2$—, —$CH_2CH_2CH_2$—, or —$CH_2CH_2CH_2CH_2$—; linear alkoxy moieties of the general form —$(CH_2)_aO$— or —$O(CH_2)_a$— where "a" is an integer from 1 to 10, including for example, —$CH_2O$— or —$OCH_2$—, —$CH_2CH_2O$— or —$OCH_2CH_2$—, —$CH_2CH_2CH_2O$— or —$OCH_2CH_2CH_2$—; —O—$(CH_2)_aO$— where "a" is as defined above; or a moiety of the form —$(CH_2)_bO(CH_2)_c$—, —$(CH_2)_bS(CH_2)_c$—, or —$(CH_2)_bNR^a(CH_2)_c$— wherein "b" and "c" are independently an integer from 0 (zero) to 10 and $R^a$ is as defined above. In preferred embodiments, $Z_1$ and $Z_2$ will comprise an oxygen atom bound to the adjacent Si atom and are therefore exemplified by radicals such as O, —$CH_2O$— or —$OCH_2$—. $Z_1$ may alternatively comprise a non-aromatic ring system together with $R_{11}$, $R_{12}$, or $R_8$ and $Z_2$ may alternatively comprise a non-aromatic ring system together with $R_7$, $R_9$, or $R_{10}$.

$R_7$ and $R_8$ are independently selected from hydrogen or unsubstituted branched or straight chain $C_1$-$C_{10}$ alkyl, alkenyl, or alkynyl group, including without limitation methyl, ethyl, propyl, isopropyl, butyl, isobutyl, t-butyl, n-pentyl, iso-pentyl, neo-pentyl, tert-pentyl, hexyl, vinyl, allyl, butenyl, pentenyl, hexenyl, propynyl, butynyl, pentynyl; cycloalkyl, heterocycloalkyl, haloalkyl, benzyl, alkyl-aryl; substituted or unsubstituted aryl or heteroaryl groups; amino, alkyl amino, dialkyl amino, hydroxyl, hydrido, carboxy, cyano, or halogen. Preferably $R_2$ and $R_3$ are both hydrogen. $R_7$ may alternatively comprise a non-aromatic ring system together with $R_{11}$, $R_{12}$, or $Z_1$.

$R_9$, $R_{10}$, $R_{11}$ and $R_{12}$ are independently selected from hydrogen, substituted or unsubstituted branched or straight chain $C_1$-$C_{10}$ alkyl, alkenyl, or alkynyl group, including without limitation methyl, ethyl, propyl, isopropyl, butyl, isobutyl, t-butyl, pentyl, hexyl, vinyl, allyl, butenyl, pentenyl, hexenyl, propynyl, butynyl, n-pentyl, iso-pentyl, neo-pentyl, tert-pentyl; cycloalkyl, heterocycloalkyl, haloalkyl, benzyl, alkyl-aryl; substituted or unsubstituted aryl or heteroaryl groups; $C_1$-$C_6$ alkoxy, amino, alkyl amino, dialkyl amino, hydroxyl, hydrido, carboxy, cyano, or halogen.

In one embodiment, the alkenyl-functionalized polymer will comprise one or more alkenyl-functionalized side chains. In this embodiment, any of $R_1$, $R_2$, $R_3$, $R_4$, $R_5$ and $R_6$ may independently be the fragment:

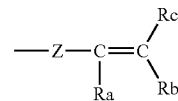

wherein Z is as defined above for $Z_1$ and $Z_2$ and $R_a$, $R_b$, and $R_c$ are independently selected from hydrogen, substituted or unsubstituted branched or straight chain $C_1$-$C_{10}$ alkyl, alkenyl, or alkynyl group, including without limitation methyl, ethyl, propyl, isopropyl, butyl, isobutyl, t-butyl, pentyl, hexyl, vinyl, allyl, butenyl, pentenyl, hexenyl, propynyl, butynyl, n-pentyl, iso-pentyl, neo-pentyl, tert-pentyl; cycloalkyl, heterocycloalkyl, haloalkyl, benzyl, alkyl-aryl; substituted or unsubstituted aryl or heteroaryl groups; $C_1$-$C_6$ alkoxy, amino, alkyl amino, dialkyl amino, hydroxyl, carboxy, cyano, or halogen.

"m" represents any integer greater than 2 and will typically be between about 3 and about 5,000 and is preferably selected to provide a polymer having a molecular weight of about 800 to about 550,000 g/mol. As will be evident to the skilled artisan, the viscosity of the alkenyl-functionalized organopolysiloxane can be varied by controlling the degree of polymerization and the ratio of T and Q structures. In this regard, suitable organosiloxane polymers will typically have a viscosity of about 5 up to about 20,000,000 centistokes.

In one currently preferred embodiment of the invention, the organosiloxane polymer comprises a polydimethylsiloxane polymer (i.e., $R_5$ and $R_6$=methyl). The polydimethylsiloxane polymer has two or more alkenyl-functionalized terminal groups or side chains.

The alkenyl-functionalized organopolysiloxane may further comprise monomers having branching points of the T or Q type. When present, the T and Q structures will typically represent less than about 50%, preferably less than about 20%, and more preferably less than about 10% of the total repeat units in the cross-linked organopolysiloxane polymer. The alkenyl-functionalized organopolysiloxane polymer may be a homopolymer defined by formula I or block, alternating, or statistical copolymer comprising the polymers of formula I. The copolymer of the alkenyl-functionalized siloxane may be a grafted or blocked copolymer of silicone acrylate, silicone polyamide, silicone polyether, fluorinated silicone, silicone polyurethane, and the like. An exemplary copolymer of the alkenyl-functionalized siloxane may be a copolymer of a divinyl-functionalized organopolysiloxane with at least one of silicone acrylate, silicone polyamide, silicone polyether, fluorinated silicone, and silicone polyurethane.

There alkenyl-functionalized siloxane component may be a straight chain, branched, cyclic, or network structure, however, straight chain or slightly branched structures are preferred. The molecular weight of the alkenyl-functionalized siloxane component is not specifically restricted, and thus the viscosity may range from low viscosity liquids to very high viscosity gums. In order for the cured product to be obtained in the form of the rubbery elastomer, it is preferred that the viscosity at be at least 100 centistokes at 25° C.

Exemplary alkenyl-functionalized siloxanes include without limitation methylvinylsiloxanes, methylvinylsiloxane-dimethylsiloxane copolymers, dimethylvinylsiloxy-terminated dimethylpolysiloxanes, dimethylvinylsiloxy-terminated dimethylsiloxane-methylphenylsiloxane copolymers, dimethylvinylsiloxy-terminated dimethylsiloxane-diphenylsiloxane-methylvinylsiloxane copolymers, trimethylsiloxy-terminated dimethylsiloxane-methylvinylsiloxane copolymers, trimethylsiloxy-terminated dimethylsiloxane-methylphenylsiloxane-methylvinylsiloxane copolymers, dimethylvinylsiloxy-terminated methyl(3,3,3-trifluoropropyl)polysiloxanes, and dimethylvinylsiloxy-terminated dimethylsiloxane-methyl-(3,3-trifluoropropyl) siloxane copolymers.

The vinyl-terminated polydimethyl siloxane polymer may, for example, have a viscosity from about 4-6, about 100, about 200, about 500, about 1,000, about 5,000, about 10,000, about 20,000, or about 60,000 cps; and may have a molecular weight of, for example, about 500-1,000, about 6,000, about 9,400, about 17,200, about 28,000, about 49,500, about 62,700, about 72,000, or about 117,000, and may, for example, comprise a percent by weight vinyl of about 7-9%, about 0.8-1.2%, about 0.4-0.6%, about 0.37-0.43%, about 0.18-0.26%, about 0.1-0.13%, about 0.08-0.12%, about 0.07-0.09%, or about 0.04-0.06%. These representative embodiments are not intended to be limiting.

The hydrosilane polymer will typically, although not necessarily, have the structure shown in Formula II:

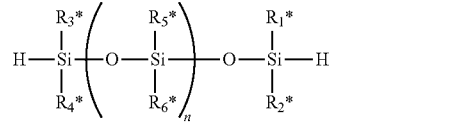

II wherein $R_1^*$, $R_2^*$, $R_3^*$, $R_4^*$, $R_5^*$, and $R_6^*$ are independently selected at each occurrence from substituted or unsubstituted branched or straight chain $C_1$-$C_{10}$ alkyl, alkenyl, or alkynyl group, including without limitation methyl, ethyl, propyl, isopropyl, butyl, isobutyl, t-butyl, pentyl, hexyl, vinyl, allyl, butenyl, pentenyl, hexenyl, propynyl, butynyl, n-pentyl, iso-pentyl, neo-pentyl, tert-pentyl; cycloalkyl, heterocycloalkyl, haloalkyl, benzyl, alkyl-aryl; substituted or unsubstituted aryl or heteroaryl groups; $C_1$-$C_6$ alkoxy, amino, alkyl amino, dialkyl amino, hydroxyl, hydrido, carboxy, cyano, or halogen; or $R_1^*$, $R_2^*$, $R_3^*$, $R_4^*$, $R_5^*$, and $R_6^*$ may each independently represent branching points in the organopolysiloxane backbone whereby D, T, or Q structures are introduced.

In one embodiment, any of $R_1^*$, $R_2^*$, $R_3^*$, $R_4^*$, $R_5^*$, and $R_6^*$ may independently be the fragment:

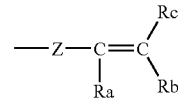

wherein Z is the same as defined above for $Z_1$ and $Z_2$ of the alkenyl-functionalized polymer and $R_a$, $R_b$, and $R_c$ are independently selected from hydrogen, substituted or unsubstituted branched or straight chain $C_1$-$C_{10}$ alkyl, alkenyl, or alkynyl group, including without limitation methyl, ethyl, propyl, isopropyl, butyl, isobutyl, t-butyl, pentyl, hexyl, vinyl, allyl, butenyl, pentenyl, hexenyl, propynyl, butynyl, n-pentyl, iso-pentyl, neo-pentyl, tert-pentyl; cycloalkyl, heterocycloalkyl, haloalkyl, benzyl, alkyl-aryl; substituted or unsubstituted aryl or heteroaryl groups; $C_1$-$C_6$ alkoxy, amino, alkyl amino, dialkyl amino, hydroxyl, carboxy, cyano, or halogen. Preferably, $R_5^*$, and $R_6^*$ are both methyl such that the polymer comprises the repeat unit of a polydimethylsiloxane (PDMS) polymer. Alternatively, $R_1^*$, $R_2^*$, $R_3^*$, and $R_4^*$ are each methyl. More preferably, $R_1^*$, $R_2^*$, $R_3^*$, $R_4^*$, $R_5^*$, and $R_6^*$ are each methyl.

Exemplary hydrosilanes include without limitation alkyltrihydrosilanes, aryltrihydro-silanes, dialkyldihydrosilanes, diaryidihydrosilanes, trialkylhydrosilanes, triarylhydrosilanes, alkylhydrosiloxanes and arylhydrosiloxanes. Special mention may be made of polymethylhydrosiloxanes, t-butyldimethylhydrosilane, triethylhydrosilane, diethyldihydrosilane, triisopropylhydrosilane and mixtures thereof.

The hydrosilane will comprise at least 2 silicon-bonded hydrogen atoms in each molecule. In practice, it has been found desirable, although not strictly necessary, to provide both polymeric components such that the sum of the number of alkenyl groups in each molecule of the alkenyl-functionalized siloxane component and the number of silicon-bonded hydrogen atoms in each molecule of hydrosilane is at least 5. Where the sum of alkenyl groups and silicon-bonded hydrogen atoms is less than 5, only a weak network structure is formed.

The hydrosilane component may be branched or straight chain, cyclic, or any combination thereof. The molecular weight of this component is not specifically restricted but is preferably between about 1 and about 100,000 daltons in order to obtain good miscibility with alkenyl-functionalized siloxane component. It is desirable, but not required, that this component be added in a quantity such that the molar ratio between the total quantity of silicon-bonded hydrogen atoms in the hydrosilane component and the total quantity of all lower alkenyl groups in alkenyl-functionalized siloxane component falls within the range of about 1.5:1 to about 20:1. In practice, it has been found difficult to obtain good curing properties when the molar ratio falls below about 0.5:1. At molar ratios above about 20:1 the resultant filaments may be undesirably hard when the cured product is heated and thus less desirable for some cosmetic applications.

The hydrosilane component may, but not necessarily, have a viscosity of about 10-15, about 25-35, or about 6,000 to 8,000 cps, and may have a wide range of suitable molecular weights, including without limitation representative embodiments having a molecular weight of about 900-1,200, or about 1,900-2,000, or about 55,000 to about 60,000, and the hydrosilane component may have a percentage of hydrogen bonded directly to silicon atoms (i.e., silane) of about 50-55% by weight, about 25-30% by weight, or about 0.5-1% by weight. These representative embodiments are not intended to be limiting.

As an optional expedient, siloxane polymers having only one alkenyl-functionalized terminal group or side chain and/or hydrosilanes having only one Si—H unit may also be added to the filament-forming compositions to impart additional control over the cross-linking density. It is within the skill in the art to determine the amounts of such optional mono-functionalized components to achieve a desired degree of cross-linking.

In this embodiment, the cross-linking agent may be any catalyst capable of affecting the addition reaction. Preferably, the catalyst is one which is capable of initiating the addition reaction below body temperature so as to achieve rapid cross-linking (i.e., about 5 seconds to about 5 minutes). Group VIII metal catalysts, including cobalt, platinum, ruthenium, rhodium, palladium, nickel, osmium and iridium catalysts, are contemplated to be suitable for the practice of this preferred embodiment. Preferably, the catalyst is a platinum, rhodium, or palladium catalyst, and more preferably, the catalyst is a platinum catalyst, including without limitation chloroplatinic acid, platinum acetylacetonate, complexes of Pt(II) with olefins, Pt(0) complexes with phosphines, $PtO_2$, $PtCl_2$, $PtCl_3$, $Pt(CN)_3$, $PtCl_4$, $H_2PtCl_6 \cdot 6H_2O$, $Na_2PtCl_4 \cdot 4H_2O$, $PtCl_2$-olefin complexes, H(PtCl3-olefin) complexes, hexamethyldiplatinum, Pt(0)-vinylsiloxanes, Pt(0) catalysts such as Karstedt's catalyst, platinum-alcohol complexes, platinum-alkoxide complexes, platinum-ether complexes, platinum-aldehyde complexes, platinum-ketone complexes and the like. Suitable rhodium catalysts include without limitation rhodium complexes such as rhodium(III) chloride hydrate and $RhCl_3(Bu_2S)_3$. Other hydrosilylation (addition) catalysts are described in, for example, U.S. Pat. Nos. 6,307,082, 5,789,334, 4,681,963, 3,715,334, 3,775,452, 3,814,730, 3,159,601, 3,220,972, 3,576,027, and 3,159,662, the disclosures of which are hereby incorporated by reference.

There is essentially no constraint on the amount of catalyst that will be present in the composition. It may be desirable to employ an amount of catalyst sufficient to enable the rapid formation of cross-linked polymers having a higher molecular weight, which are more adapted for drawing into a filament.

Suitable commercially available hydrosilylation (addition) cross-linking compositions which may be readily formulated into such one or two-part systems as discussed in Section B below, include without limitation Dow Corning 8-8024 Base and Dow Corning 8-8024 Curing Agent, Dow Corning 7-9800 Part A&B Soft Skin Adhesive™, and Dow Corning 7-6800 Part A&B Silky Touch™, Dow Corning's Silastic® Liquid Silicone Rubber (LSR), Dow Corning C6 LSR serial, Silastic® Q7 serial, Silastic® 590 LSR Part A&B, Silastic® 591 LSR Part A&B, Silastic® LSR 9151-200P, Silastic® LSR 9451-1000P, and Silastic® 5-8601 LSR fluorosilicone materials. Similar LSR products are available from General Electric Advanced Materials under the names Silopren® LSR, LIM® LSR, LSR Topcoat, and Addisil®.

ii. Filament Forming Components Having In-Situ Silicone Condensation Cross-Linking In an alternative embodiment, the cross-linkable polymers may comprise a siloxane polymer, having at least one side chain or terminal group comprising an alkoxy functional group, and is capable of undergoing a condensation reaction in the presence of water and a catalyst, which serves as the cross-linking agent.

In the presence of water, the siloxane polymer undergoes metal catalyzed in situ cross-linking by condensation of the alkoxy terminated moieties. Typically, suitable siloxane polymers are organopolysiloxanes having the structure shown in formula III:

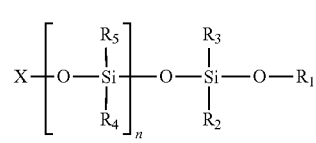

wherein $R_1$ is a branched or straight chain $C_1$-$C_{10}$ alkyl group, including without limitation methyl, ethyl, propyl, isopropyl, butyl, isobutyl, or t-butyl. With due regard for the kinetics of the polycondensation reaction, $R_1$ is preferably a methyl or ethyl group, and most preferably $R_1$ is a methyl group, so as to provide a highly reactive alkoxy terminus for efficient and rapid cross-linking.

$R_2$ and $R_3$ are independently selected from branched or straight chain alkoxy groups, as exemplified by methoxy and ethoxy; substituted or unsubstituted branched or straight chain $C_1$-$C_{10}$ alkyl, alkenyl, or alkynyl group, including without limitation methyl, ethyl, propyl, isopropyl, butyl, isobutyl, t-butyl, n-pentyl, iso-pentyl, neo-pentyl, tert-pentyl, hexyl, vinyl, allyl, butenyl, pentenyl, hexenyl, propynyl, butynyl, pentynyl; cycloalkyl, heterocycloalkyl, haloalkyl, benzyl, alkyl-aryl; substituted or unsubstituted aryl or heteroaryl groups; amino, hydroxyl, hydrido, carboxy, cyano, or halogen. Preferably $R_2$ and $R_3$ are independently selected from methoxy, phenyl, amino, hydroxyl, and carboxy. It will be recognized that, in the case where $R_2$ and/or $R_3$ are alkoxy moieties, the possibility exists for multiple condensation cross-linking reactions to occur. In this manner, so-called "T" and "Q" functionalities can be introduced into the polymer through cross-linking.

$R_4$ and $R_5$ are independently selected at each occurrence from substituted or unsubstituted branched or straight chain $C_1$-$C_{10}$ alkyl, alkenyl, or alkynyl group, including without limitation methyl, ethyl, propyl, isopropyl, butyl, isobutyl, t-butyl, pentyl, hexyl, vinyl, allyl, butenyl, pentenyl, hexenyl, propynyl, butynyl, n-pentyl, iso-pentyl, neo-pentyl, tert-pen tyl; cycloalkyl, heterocycloalkyl, haloalkyl, benzyl, alkyl-aryl; substituted or unsubstituted aryl or heteroaryl groups; $C_1$-$C_6$ alkoxy, amino, hydroxyl, hydrido, carboxy, cyano, or halogen. Preferably $R_4$ is methyl. Alternatively, $R_4$ and/or $R_5$ may be, at one or more occurrences, a —$OR_1$, group, where observation that this alternative preferred embodiment does not embrace alkylene trialkoxy terminated polysiloxanes.

The organosiloxane polymer condensation reaction is illustrated below in the non-limiting case of a polydimethylsiloxane polymer having a methoxy-functionalized terminus.

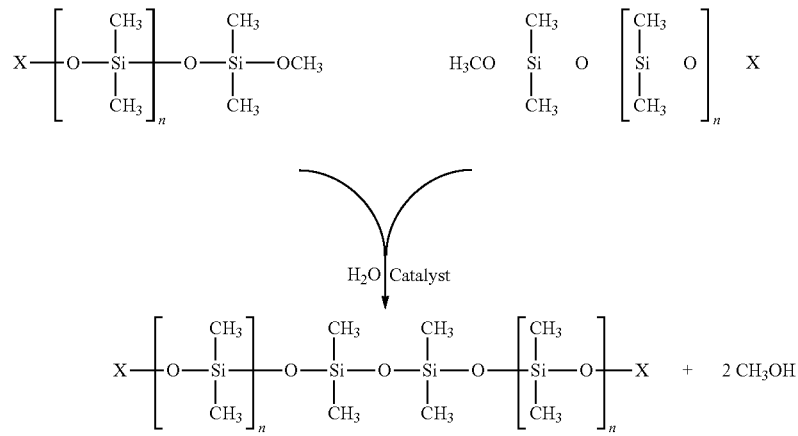

$R_1$ is as defined above, to thereby introduce a highly reactive alkoxy terminus for efficient and rapid cross-linking.

"X" represents any chain terminating group, including without limitation substituted or unsubstituted branched or straight chain $C_1$-$C_{20}$ alkyl, alkenyl, or alkynyl group, including without limitation methyl, ethyl, propyl, isopropyl, butyl, isobutyl, t-butyl, pentyl, hexyl, vinyl, allyl, butenyl, pentenyl, hexenyl, propynyl, butynyl, n-pentyl, iso-pentyl, neo-pentyl, tert-pentyl; cycloalkyl, heterocycloalkyl, haloalkyl, benzyl, alkyl-aryl; substituted or unsubstituted aryl or heteroaryl groups; alklysilyl, dialkylsilyl and trialkylsilyl, as exemplified by trimethylsilyl and triethylsilyl. Alternatively, X may be each of the foregoing being optionally substituted with one or more functional groups including without limitation, a group as defined by $R_1$, thereby introducing a highly reactive alkoxy terminus for efficient and rapid cross-linking.

"n" represents any integer greater than 2 and will typically be between about 2 and about 5,000 and is preferably selected to provide a polymer having a molecular weight of about 800 to about 550,000 g/mol. As will be evident to the skilled artisan, the viscosity of the organosiloxane polymer can be varied by controlling the degree of polymerization and the ratio of T and Q structures. In this regard, suitable organosiloxane polymers will typically have a viscosity of about 5 up to about 20,000,000 centistokes.

The polymer may further comprise monomers having branching points of the T or Q type. When present, the T and Q structures will typically represent less than about 50%, preferably less than about 20%, and more preferably less than about 10% of the total repeat units in the cross-linked organopolysiloxane polymer.

The organosiloxane polymer may be a homopolymer defined by formula III or block, alternating, or statistical copolymer comprising the polymers of formula III.

In one currently preferred embodiment of the invention, the organosiloxane polymer comprises a polydimethylsiloxane polymer (i.e., $R_4$ and $R_5$=methyl). Preferably, the polydimethylsiloxane polymer has one or more methoxy-functionalized terminal groups or side chains (i.e., $R_1$=methyl and/or one or more of $R_2$, $R_3$, $R_4$, and $R_5$=methoxy). In selecting $R_1$, $R_2$ and $R_3$ the skilled artisan will be further guided by the In this embodiment, the cross-linking agent may be any catalyst capable of affecting the condensation reaction. Preferably, the catalyst is one which is capable of initiating the condensation reaction at or below body temperature so as to achieve rapid cross-linking (i.e., about 5 seconds to about 5 minutes). Tin catalysts, titanium catalysts and zirconium catalysts have been found to be suitable for the practice of this alternative preferred embodiment.

Tin catalysts are preferably used in the case where $R_2$ and/or $R_3$ are alkoxy moieties. Suitable tin catalysts include without limitation diorganotin dicarboxylates, including, for example, dibutyltin dilaurate, dioctyltin maleate, diorganotin oxides in silicic acid esters, and the like.

Suitable titanium catalysts include without limitation alkyl titanates, including, for example, methyl titanate, ethyl titanate, n-propyl titanate, isopropyl titanate, tetraisopropyl titanate, n-butyl titanate, tetrabutyl titanate, n-butyl titanate polymer, t-butyl titanate, 2-ethylhexyl titanate, and mixed alkyl titanates; titanate esters, titanium acetylacetonates, acid titanium chelates including lactic acid titanium chelate, alkoxy titanates, alchohol titanium complexes, diisobutyl bis(ethyl-acetoacetate) titanate, diisopropyl bis(acetyl-acetonate) titanate, diisopropyl bis(ethyl-acetoacetate) titanate, and the like.

Suitable zirconium catalysts include the alkyl zircoates and zirconate esters, for example, methyl zirconate, ethyl zircoate, n-propyl zircoate, isopropyl zircoate, n-butyl zircoate, 2-ethylhexyl zircoate, tetra n-butyl zircoate, tetra n-propyl zircoate, mixed alkyl zircoate esters and the like.

There is essentially no constraint on the amount of catalyst that will be present in the composition. It may be desirable to employ an amount of catalyst sufficient to enable the rapid formation of cross-linked polymers.

A class of industrial products suitable for use are the Tyzor® (DuPont) line of titanium and zirconium catalysts. Most preferred are t-butyl titanate and t-butyl zirconate because they have been found to possess the best balance of moisture resistance and reactivity.

Water is essential to the condensation reaction and therefore the reactive organosiloxane polymer must be kept anhydrous prior to application, or alternatively, must be kept apart from the catalyst prior to application.

B. Filament Forming Systems

In accordance with another aspect of the invention, filament forming systems comprising the filament forming components are provided. The filament forming systems are designed to prevent the cross-linking reaction from occurring prior to application and yet provide convenient means for application. The filament forming systems are generally one-part systems or two-part systems and react to form cosmetic filaments in situ on keratin fibers.

i. One-Part Systems

In a one-part system where the cross-linkable polymers comprise an alkenyl-functionalized siloxane polymer and a hydrosilane capable of undergoing metal catalyzed cross-linking through the addition reaction of hydrosilane to the alkenyl-functionalized terminal groups or side chains of the siloxane polymer, the cross-linkable polymers and the catalyst will necessarily be packaged together. Various methods for preventing polymerization reaction from occurring prior to application may be envisaged, all of which are contemplated to be within the scope of the invention. However, particular embodiments described below are consider to be currently preferred.

In one interesting implementation of the invention, the filament forming system is a one-part, multi-use system having a continuous phase comprising the alkenyl-functionalized siloxane dissolved in a carrier medium and a disperse phase comprising a plurality of microcapsules dispersed in the continuous phase. Because it is necessary to prevent the three components (alkenyl-functionalized siloxane, hydrosilane and catalyst) from coming into contact prior to use, either the hydrosilane or the catalyst may be disposed within the plurality of microcapsules. Preferably, the catalyst is contained within the microcapsules. Only when the microcapsules are ruptured or otherwise degraded do the three components come into intimate contact and thus initiate the cross-linking reaction.

As is well known in the art, encapsulating materials can be selected which will release the catalyst upon exposure to moisture, pH change, temperature change, solubility change, or mechanical shear. Suitable encapsulating materials and methods of preparing encapsulated materials, such as spray drying, extrusion, coacervation, fluidized bed coating, liposome entrapment and others, are disclosed in, for example, U.S. Patent Application Publication No. 2005/0000531 to Shi; Uhlmann, et al., "Flavor encapsulation technologies: an overview including recent developments" *Perfumer and Flavorist*, 27, 52-61, 2002; and "Selection of Coating and Microencapsulation Processes" by Robert E. Sparks and Irwin Jacobs in *Controlled-Release Delivery Systems for Pesticides*, Herbert B. Scher ed., Marcel Dekker, New York, N.Y., 1999, pp. 3-29, the contents of which are hereby incorporated by reference. Moisture sensitive microcapsules will suffer the disadvantage of requiring anhydrous conditions prior to use and are therefore less preferred than microcapsules which release their contents by other mechanisms when employed in re-usable formulations, where ambient moisture may be introduced into the packaging during use.

Additionally, the one-part system comprising an alkenyl-functionalized siloxane polymer, a hydrosilane and a catalyst may be formulated where all three components are present in admixture along with a hydrosilylation inhibitor, which prevents the crosslinking reaction from occurring prior to the occurrence of a trigger event, such as, but not limited to, evaporation or sublimation of the inhibitor, temperature change, pH change and photo-activation. Non-limiting examples of hydrosilylation inhibitors are described in U.S. Pat. Nos. 3,445,420, 4,256,870, 4,465,818, 4,562,096, and 5,629,387, the disclosures of which are hereby incorporated by reference. It is well within the skill in the art to select a suitable inhibitor.

The one-part anhydrous systems may be packaged in any conventional manner, including bottles, tubes, tubs, and the like. When so packaged the composition may be applied to the biological surfaces with any type of applicator known in the art, including, sprays, swabs, brushes, towelets, and applicator tips inegral with the package.

Preferably, an inert carrier is also present to solubilize the alkenyl-functionalized organosiloxane and provide for efficient application. There is essentially no constraint on the selection of carrier. However, the carrier should ideally be unreactive in the presence of the alkenyl-functionalized organosiloxane, and compatible with a cosmetic or personal care product. The carrier may be aqueous or anhydrous. The carrier will typically comprise from about 10% to about 90% by weight of the filament forming formulation, and more typically between about 30% and about 80% by weight. In preferred embodiments, the carrier comprises between about 50% and about 70% by weight of the filament forming formulation.

In certain embodiments, the carrier may a hydrophilic solvent such as, for example, lower alcohols and polyhydric alcohols. Preferably, the carrier should be anhydrous, unreactive in the presence of the cross-linkable polymers and cross-linking agent, and compatible with a cosmetic or personal care product. The carrier may be a hydrophobic solvent, including, for example, volatile and non-volatile oils. Volatiles oils generally have a vapor pressure of at least about 2 mm of mercury at 20° C., while non-volatile oils typically have a vapor pressure of less than about 2 mm of mercury at 20° C.

Suitable volatile oils include, for example, (1) hydrocarbon oils, including without limitation, $C_8$-$C_{20}$ hydrocarbons, such as isododecane, and (2) silicone oils, including without limitation, (a) linear silicones, such as hexamethyldisiloxane (HMDS) and polydimethylsiloxane (dimethicone) polymers, and (b) cyclic silicones, such as cyclodimethicones. Suitable non-volatile dimethicone polymers are available from Dow Corning under the name Dow Corning 200® Fluid and have viscosities ranging from 5 to 600,000 centistokes.

Other suitable volatiles oils include straight or branched chain paraffinic hydrocarbons. Preferably, the paraffinic hydrocarbons have 5 to 40 carbon atoms. More preferably, the paraffinic hydrocarbons have 8 to 20 carbon atoms. Most preferably, the paraffinic hydrocarbons may be $C_8$-$C_{20}$ isoparaffins as described in, for example, U.S. Pat. Nos. 3,439,088 and 3,818,105, the contents of which are hereby incorporated by reference.

Non-polar, volatile oils particularly useful in the present invention are disclosed, for example, in Cosmetics, Science, and Technology, Vol. 1, 27-104 edited by Balsam and Sagarin, 1972. The non-polar, volatile oils useful in the present invention may be either saturated or unsaturated, have an aliphatic character and be straight or branched chained, or contain alicyclic or aromatic rings. Examples of preferred non-polar, volatile hydrocarbons include polydecanes such as isododecane and isodecane, including for example, Permethyl-99A (Presperse Inc.) and the $C_7$-$C_8$ through $C_{12}$-$C_{15}$ isoparaffins such as the Isopar Series available from Exxon Chemicals.

Suitable non-polar, volatile liquid silicone oils are disclosed in U.S. Pat. No. 4,781,917, herein incorporated by reference in its entirety. Additional volatile silicones materials are described in Todd et al., "Volatile Silicone Fluids for Cosmetics", Cosmetics and Toiletries, 91:27-32 (1976), herein incorporated by reference in its entirety. Linear volatile silicones generally have a viscosity of less than about 5 centistokes at 25° C., whereas the cyclic silicones have viscosities of less than about 10 centistokes at 25° C. Examples of cyclomethicones of varying viscosities include Dow Corning 200, Dow Corning 244, Dow Corning 245, Dow Corning 344, and Dow Corning 345, (Dow Corning Corp.); SF-1204 and SF-1202 Silicone Fluids (G.E. Silicones), GE 7207 and 7158 (General Electric Co.); and SWS-03314 (SWS Silicones Corp.).

Non-volatile oils suitable as an inert carrier in the present invention may include, without limitation, naturally occurring glyceryl esters of fatty acids or triglycerides, such as lanolin oil, triisocetyl citrate, $C_{10}$-$C_{18}$ triglycerides, coconut oil, corn oil, palm oil, sunflower seed oil and synthetic or semi-synthetic glyceryl esters, such as modified fatty acid mono-, di-, and triglycerides. Useful modified glycerides include, for example, acetylated castor oil, glyceryl stearate, glycerol dioleate, glyceroldistearate, glycerol myristate, PEG castor oils, PEG glycerol oleates, PEG glycerol stearates and the like. Other non-volatile oils useful in the present invention are essentially non-volatile polysiloxanes, paraffinic hydrocarbon oils, and mixtures thereof. Notably, exemplary non-volatile oils of particular interest are hydrogenated polyisobutene, squalene, fatty esters, fatty alcohols, petrolatum and mineral oil.

Suitable polysiloxanes useful as a carrier in the present invention are selected from the group consisting of polyalkylsiloxanes, polyarylsiloxanes, polyalkylarylsiloxanes, polyethersiloxane copolymers, and mixtures thereof. Special mention may be made of polydimethyl siloxanes having viscosities of from about 1 to about 600,000 centistokes at 25° C., including without limitation the Viscasil series of polyalkylsiloxanes (General Electric Company) and the Dow Corning 200 series (Dow Corning Corp.). Suitable polyalkylarylsiloxanes include polymethylphenyl siloxanes having viscosities of from about 15 to about 65 centistokes at 25° C. such as, for example, those available as SF 1075 methylphenyl fluid (General Electric Company) and 556 Cosmetic Grade Fluid (Dow Corning Corp.). Useful polyethersiloxane copolymers include, without limitation, a polyoxyalkylene ether copolymer having a viscosity of about 1200 to 1500 centistokes at 25° C., including for example SF1066 organosilicone surfactant (General Electric Company).

In a one-part system, where the cross-linkable polymers comprise an alkoxy-functionalized polymer capable of cross-linking in the presence of catalyst and water through polycondensation of the alkoxy-terminal groups, the reactive organosiloxane polymer and catalyst will necessarily be packaged together. Various methods for preventing the cross-linking reaction from occurring prior to application may be envisaged, all of which are contemplated to be within the scope of the invention. However, particular embodiments described below are consider to be currently preferred.

In one embodiment, the reactive organosiloxane polymer and catalyst are packaged together in an anhydrous state. There is essentially no constraint on the amount of catalyst that will be present in the composition. Typically, the catalyst will be present in a ratio to the organosiloxane polymer of about 1:1,000 to about 1:5. It may be desirable to employ an amount of catalyst toward the higher end of this range to account for the fact that diffusion in a viscous composition is limited. A preferred range is about 1:100 to about 1:10.

A one-part silicone condensation cross-linking system is commercially available as Dow Corning 7-5300 Film-in-Place Coating. One-part Room Temperature Vulcanising (RTV) Rubbers from GE and Dow Corning are also contemplated to be useful silicone condensation cross-linking system for the one-part systems of the invention. Such single part systems consist of a polydialkylsiloxane with terminal hydroxyl groups, which are reacted with organosilicone cross-linking agents. This operation is carried out in a moisture-free environment and results in the formation of a tetrafunctional structure. Curing takes place when materials are exposed to moisture. Atmospheric moisture is sufficient to trigger the reaction. For example, RTV167, TSE392-C, and XE11-B1002 from GE are one-part room temperature condensation cross-linking systems.

The one-part anhydrous systems may be packaged in any conventional manner, including bottles, tubes, tubs, and the like. However, such products may be limited to one-time use because ambient moisture introduced into the packaging through opening and closing will initiate the cross-linking reaction in the unused portion. Upon application to keratin fibers, the compositions will rapidly polymerize on the keratin fibers due to the presence of moisture in the air or on the surface to form a cross-linked filament with excellent adherent properties.

In such one-part systems requiring anhydrous conditions, multi-use systems may also be prepared by incorporating the filament forming compositions in sealed dispensers which prevent ambient moisture from entering the packaging during application. In this regard, particular mention may be made of the cosmetic dispensers disclosed in U.S. Pat. Nos. 5,533,823, 5,984,554, and 5,342,134, the disclosure of which are hereby incorporated by reference. The one-part system may be solvent-free or comprises one or more cosmetically acceptable carriers, as described above, in which the polymer is soluble or dispersible.

While the foregoing anhydrous one-part systems are within the scope of the invention, it is preferred to provide one-part systems which do not depend on the maintenance of an anhydrous condition. Such systems will provide multi-use products which do not require special packaging to avoid the introduction of moisture. In one interesting implementation of the invention, the filament forming system is a one-part, multi-use system comprising a continuous phase of reactive organosiloxane polymer dissolved in a carrier medium and a disperse phase comprising a plurality of microcapsules, in a similar manner as described above, having the catalyst encapsulated therein. Because the catalyst and organosiloxane polymer are prevented from coming into intimate contact by virtue of the encapsulant, the cross-linking reaction is prevented. Only when the microcapsules are ruptured or otherwise degraded does the catalyst contact the polymer.

ii. Two-Part Systems

In another embodiment of the invention where the cross-linkable polymers comprise an alkenyl-functionalized siloxane polymer and a hydrosilane capable of undergoing metal catalyzed cross-linking through the addition reaction of hydrosilane to the alkenyl-functionalized terminal groups or side chains of the siloxane polymer, the hydrosilane and the catalyst are physically separated prior to use. The system may be in the form of a first component comprising the alkenyl-functionalized organosiloxane and catalyst and a second component comprising the hydrosilane and optionally additional alkenyl-functionalized organosiloxane. Both the first and second components may further comprise a carrier material, as described above.

The first and second compositions may be packaged separately, for example in two containers, bottles, tubes, and the like, or may be packaged in one container having a physical partition which prevents the first and second components from coming into contact as described in, for example, U.S.

Patent Application Publication No. 2004/0165935 and U.S. Design Pat. Nos. D449,224, D326,606 and U.S. Pat. Nos. 6,789,971, 6,247,586, 5,318,203, 4,196,808 and 3,757,782, the contents of which are hereby incorporated by reference.

In use, it is preferred to first apply the component comprising the alkenyl-functionalized organosiloxane and catalyst to a surface as a base coat. Thereafter, the component comprising the hydrosilane is applied as a top coat over the base coat. The base and top coats are applied onto the surface sequentially with a mixing ratio from about 1:1 to about 5:1. Alternatively, the first and second components may be mixed immediately prior to use and applied as one coating to the surface.

Alternatively, the first and second parts are separated by a dual component package, such as a dual cartridge with a mixer nozzle and applied as a single step. The skilled artisan will recognize that the foregoing embodiments are merely illustrative and all systems in which the three components are prevented from reacting prior to use are considered to be within the scope of the invention.

The first or second components may optionally comprise an agent for accelerating the hydrosilylation (addition) reaction. Such agents are well known in the art and disclosed in, for example, U.S. Pat. No. 6,303,728, the disclosure of which is hereby incorporated by reference.

Two-part Room Temperature Vulcanising (RTV) Rubbers from GE and Dow Corning under the names RTV615 and RTV627 is an example of a commercially available two-part hydrosilylation (addition) cross-linking system.

In another embodiment, the cross-linkable polymers may comprise a reactive organosiloxane polymer which is capable of undergoing a condensation reaction in the presence of water and a cross-linking catalyst. The reactive organosiloxane polymer and the catalyst are physically separated prior to use. The system may be in the form of a first component comprising the reactive organosiloxane polymer and a second component comprising the catalyst. The first and second components may be packaged separately, as described above. In this embodiment, it is not necessary to maintain anhydrous conditions in either component. Both the first and second components may further comprise a carrier material, as described above.

In use, it is preferred to first apply the component comprising the reactive organosiloxane to a surface as a base coat. Thereafter, the component comprising the catalyst is applied as a top coat over the base coat. The base and top coats are applied onto the surface sequentially with a mixing ratio from about 1:1 to about 5:1. Alternatively, the first and second components may be mixed immediately prior to use and applied as one coating to the surface.

A suitable two-part silicone condensation cross-linking system is commercially available as Dow Corning 7-5310 Base and Dow Corning 7-5311 Curing Agent, which is an in-situ cure elastomer film former used in health care industry for scar or wound healing.

C. Cosmetic Formulations

The filament forming systems may be useful in a variety of cosmetic and personal care products, including without limitation, mascara formulations, eyelash or eyebrow lengthening or volumizing compositions, hair care products, and other cosmetic products where durable, flexible cosmetic filaments are desired. In one embodiment, a cosmetic formulation is provided comprising the in situ filament-forming systems of the invention. The cosmetic formulation is expected to exhibit a considerable degree of wear-resistance, water-resistance and oil-resistance. In a preferred embodiment, the cosmetic filaments formed from the cosmetic formulation is expected to remain on the keratin fibers and for at least 8 hours. More preferably, the cosmetic formulation is expected to remain on the keratin fibers for at least 12 hours. Even more preferably, the cosmetic formulation is expected to remain on the keratin fibers for at least 24 hours. Most preferably, the cosmetic formulation is expected to remain on the keratin fibers for at least 1 day under normal wear conditions.

The cosmetic formulations may optionally comprise one or more coloring agents which may be added to the continuous phase of the one-part systems and at least one of the first and second compositions of the two-part systems. The coloring agents may be at least one of a pigment, a pearlescent agent, or a colorant. Preferably, coloring agents may be present in the composition in an amount from about 1 weight % to about 25 weight % of the total weight of the composition, and more preferably in an amount from about 1 to about 15 weight %.

It is within the skill in the art to choose coloring agents and combinations of coloring agents to produce a desired color. Pigments may be present in the composition in an amount from about 1 weight % to about 25 weight % of the total weight of the composition, and preferably in an amount from about 1 to about 15 weight %. Suitable pigments may include titanium dioxide, zinc oxide, iron oxide, chromium oxide, ferric blue, mica, barium, strontium, calcium or aluminum lakes, ultramarines, carbon black and others. Suitable colorants include include D&C Green #3, D&C Yellow #5, D&C Blue #1 and the like. Pearlescent agents, which are iridescent particles, modify the texture of the composition and may include, for example, particles produced by certain molluses in their shell or synthesized pearlescent particles.

Various fillers may be added to reinforce the filament forming systems. When present, fillers may be added to the continuous phase of the one-part systems and at least one of the first and second compositions of the two-part systems. In a two-part system, the fillers are preferably added to both the first and second compositions. Suitable fillers include without limitation silica, treated silica, talc, zinc stearate, mica, kaolin, Nylon powders such as, for example, Orgasol™, polyethylene powder, Teflon®, starch, boron nitride, copolymer microspheres such as Expancel™ (Nobel Industries), Polytrap™ (Dow Corning) and silicone resin microbeads (Tospearl™ from Toshiba), and the like.

Additional pigment/powder fillers include, but are not limited to, inorganic powders such as gums, chalk, Fuller's earth, kaolin, sericite, muscovite, phlogopite, synthetic mica, lepidolite, biotite, lithia mica, vermiculite, aluminum silicate, starch, smectite clays, alkyl and/or trialkyl aryl ammonium smectites, chemically modified magnesium aluminum silicate, organically modified montmorillonite clay, hydrated aluminum silicate, fumed aluminum starch octenyl succinate barium silicate, calcium silicate, magnesium silicate, strontium silicate, metal tungstate, magnesium, silica alumina, zeolite, barium sulfate, calcined calcium sulfate (calcined gypsum), calcium phosphate, fluorine apatite, hydroxyapatite, ceramic powder, metallic soap (zinc stearate, magnesium stearate, zinc myristate, calcium palmitate, and aluminum stearate), colloidal silicone dioxide, and boron nitride; organic powder such as polyamide resin powder (nylon powder), cyclodextrin, methyl polymethacrylate powder, copolymer powder of styrene and acrylic acid, benzoguanamine resin powder, poly(ethylene tetrafluoride) powder, and carboxyvinyl polymer, cellulose powder such as hydroxyethyl cellulose and sodium carboxymethyl cellulose, ethylene glycol monostearate; inorganic white pigments such as magnesium oxide.

In an interesting embodiment, coloring agents (e.g., pigment, colorant or pearlescent) may be coated or surface treated to enhance shine or gloss. For example, coloring agents may be coated or surface treated with one or more compatibilizers to aid in dispersion in an aqueous phase and/or a wax phase. In a particular embodiment where the filament forming systems include silicone polymers, such as, for example, organopolysiloxanes, the pigments and/or colorants are preferably surface treated with dimethicone copolyol.

In other embodiments, the compositions may be clear or substantially clear. In these embodiments, the compositions will not comprise colorants, or will comprise very low levels of colorants, e.g., less than about 1% by weight. Thus, one embodiment of the invention provides composition for the in situ formation of a clear filament on a keratin fiber, wherein the composition is free or substantially free of colorants.

The compositions of the invention may optionally comprise other active and inactive ingredients typically associated with cosmetic and personal care products, in particular mascara and eyelash products. These ingredients may be added to the continuous phase of the one-part systems and at least one of the first and second compositions of the two-part systems. The nature of these other ingredients and their amounts should preferably be suitable for formulating a stable eyelash product which forms cosmetic filaments in situ on keratin fibers. Preferably, these other ingredients include at least one bioactive ingredient for improving the keratin fiber. It is within the skill in the art to choose additional active and/or inactive ingredients for an eyelash product. Suitable other ingredients include, but are not limited to, amino acids, antioxidants, chelating agents, colorants, depigmenting agents, emollients, emulsifiers, eyelash protectants, excipients, eyelashes penetration enhancers, fillers, fragrances, gelling agents, humectants, hypopigmenting agents, minerals, moisturizers, photostabilizing agents, preservatives, stabilizers, staining agents, surfactants, thickeners, viscosity and/or rheology modifiers, vitamins, waxes and mixtures thereof. The other ingredients may be present in an amount of about 0.01 weight % to about 20 weight % of the total weight of the composition.

B. Method of Forming In Situ a Cosmetic Filament

The present invention provides a method for lengthening and/or volumizing keratin fibers, particularly eyelashes, comprising applying to the keratin fibers a cosmetic formulation comprising one or more cross-linkable polymers, drawing out a portion of the polymers beyond a terminal end of the keratin fiber while the polymers are in a fluid or partially fluid state, and allowing the polymers to cure or set, forming a solid filamentous extension on the keratin fiber. The term "fluid or partially fluid state" as used herein refers to a viscous intermediate, wherein the cross-linkable polymers are in intimate contact and have begun cross-linking, but has not yet cured to a solid. FIG. 1 illustrates an exemplary method for lengthening and/or volumizing keratin fibers according to the present invention. The cosmetic formulation of the present invention comprises the filament forming systems described above, which are generally one-part systems or two-part systems.

For a one-part system, the cosmetic formulation comprises a single composition. The cosmetic formulation is applied to keratin fibers, particularly eyelashes 104 using any type of applicator, such as a conventional mascara brush. In a preferred embodiment, a cosmetic formulation 102, comprising a filament forming system, is brushed onto the eyelashes 104 using a mascara brush 106. The mascara brush 106 may be in any shape, for example, U.S. Pat. Nos. 6,450,177 and 6,016,815, the contents of which are hereby incorporated by reference. The cosmetic formulation 102 is preferably applied to the eyelashes 104 with an outward, extending motion in a direction of the extension of the eyelashes 104, which is away from the eyes. As the cosmetic formulation 102 is applied onto the eyelashes 104, the filament forming system becomes be activated by the occurrence of a trigger event, such as, but not limited to, evaporation or sublimation of the inhibitor, temperature change, pH change and photo-activation. Upon activation, the functional groups of the cross-linkable polymers react in situ, either directly with one another or with a monomeric cross-linking agent which in turn cross-links the polymeric chains, to form a higher molecular weight cross-linked polymer, which may be drawn into cosmetic filaments 108 on the keratin fibers.

For a two-part system, the cosmetic formulation 102 comprises two separate compositions. The two compositions are each applied in a similar manner as described above. The first composition is preferably applied first to the keratin fiber and used as a base coat, whereas the second composition is preferably applied to the keratin fiber subsequent to the first composition as a top coat. As the first composition mixes with the second composition, the cross-linkable polymers react in situ to form a higher molecular weight cross-linked polymer, which may be drawn into cosmetic filaments 108 on the keratin fibers.

While it is preferred that the first composition is applied first to the keratin fiber, in an alternative embodiment, the second composition may be applied first to the keratin fiber and followed by an application of the first composition. In another alternative embodiment, the first and second compositions may be mixed immediately prior to use and applied in the same manner as the one-part system.

The cosmetic filaments 108 are drawn from the cross-linkable polymers while the polymers are in a fluid or partially fluid state and allowed to cure or set, forming solid filamentous extensions on the keratin fibers. Preferably, the cosmetic filaments are elastomeric and flexible. It is also preferred that the cosmetic filaments demonstrate good adhesion to the keratin fibers.

In addition, the cosmetic filaments 108 may preferably be extended to a length about 0.01 mm to about 20 mm or about 1 inch or more beyond a terminal end of the keratin fiber. When applied as an eyelash extender, it is preferred that the filament extend at least about 0.5 mm, or at least about 1 mm, or at least about 1.5 mm, or at least about 2 mm beyond the terminal end of the lash. Typically, the cosmetic filaments 108 are extended to a length about 0.01 mm to about 10 mm beyond a terminal end of the eyelash. When the filaments are employed to extend other keratin fibers, such as the hair of the head, it may be possible to form extension of 1 inch or more, including, for example, extenstion of at least about 1.5 inches or at least about 2 inches or more. Where reference is made herein to the length of the filament, it will be understood that the length refers to the filament in a straightened condition, regardless of whether the filament is straight, arched, or curled.

In a particular embodiment, following application of the cosmetic formulation 102 to the eyelashes 104, the applicator, preferably a mascara brush 106, may brush the cosmetic formulation 102 in a direction of the extension of the eyelashes 104, to draw out the cross-linkable polymers while the polymers are in a fluid or partially fluid state. The mascara brush 106, may be used to brush the applied cosmetic formulation 102 for a single pass or for multiple passes. Preferably, the applied cosmetic formulation 102 is brushed at least once. More preferably, the applied cosmetic formulation 102 is brushed at least twice. Most preferably, the applied cosmetic formulation 102 is continuously brushed until the cosmetic filaments 108 are formed, dried and set. The mascara formulation 102 may be dried, for example, by evaporation of the inert carrier, such as a solvent, and other volatiles. After the polymer is cured to form the hardened filament, the ends of the filaments may be trimmed with scissors or the like to achieve a uniform edge.

The cosmetic formulations may be applied to the keratin fibers as often as needed to maintain the desired length. For a one part system, a single composition is applied to the keratin fibers a first time. Subsequently, the single composition may be applied for at least one additional time. Before a subsequent application, a previous application of the single composition is allowed to set or dry. For a two part system, the first and the second compositions may be mixed and applied a plurality of times in a similar manner as the one part system. In another embodiment, the first and second compositions may be alternately applied onto the keratin fiber until a desired length or volume, allowing a previous application to set or dry before applying a subsequent application. Notably, to achieve added length or volume for eyelashes, the cosmetic formulation may be applied onto the eyelashes a plurality of times, in the manners described above, to compound the lengthening and/or volumizing effect of the cosmetic formulation.

As discussed above, the cosmetic formulation is expected to exhibit a considerable degree of wear-resistance, water-resistance and oil-resistance. Nonetheless, periodic re-application may be necessary in the normal course wear as the cosmetic filaments may eventually detach from the keratin fibers.

C. Deformation of the Filament Fibers

The cosmetic filaments formed by the cosmetic formulation of the present invention may be, without limitation, straight, arched, or curled. In one embodiment, the cosmetic formulation comprising the filament forming systems holds eyelashes in an arched shape and/or provides curled cosmetic filaments, wherein the concave side of the arched shape is away from the eyes, and thereby enhancing and/or emphasizing the appearance of eyelashes. Mechanical force may be applied to the resultant cosmetic filaments to curl the filaments or to alter the shape of the filaments to an arched or curled shape.

When sufficient mechanical force is applied to a material, the material may change shape, or deform, as a response to the applied force. The mechanical force may be applied in a number of forms: shear force, tensile force, compressive force, torsional force, or a combination thereof. Depending on the amount of force applied, the material may undergo elastic deformation, plastic deformation or fracture. For a weak applied force, the material undergoes elastic deformation, which is a reversible and temporary shape change. The applied force is stored within the material as recoverable elastic energy. Once the applied force is removed, the material returns to its original shape. Elastomeric materials (e.g., rubber or organosiloxane polymers) by definition retain elastic properties throughout a wide range of applied stresses.

As the applied stress increases, the material transitions from having elastic properties to having inelastic, or plastic (and also referred to as viscous), properties. A material that is subject to an increased amount of stress beyond that of the transitional point undergoes plastic deformation, which is an irreversible shape change. The amount of stress beyond that of the transitional point is dissipated as viscous loss. A material must first undergo elastic deformation before reaching plastic deformation. Therefore, once the applied stress is removed, a material under plastic deformation partially returns to its original shape and maintains a portion of the shape change. Applied stress further increased beyond a critical point irreversibly fractures or breaks the material into a plurality of pieces.

In one embodiment, mechanical force may be applied to irreversibly deform, but not fracture, the filaments. In response to the stress, the cosmetic filament is expected to undergo plastic deformation. Upon release, the cosmetic filament retains a portion of the deformation and becomes curled. The cosmetic filaments of this particular embodiment are expected to be flexible, not brittle. Therefore, these cosmetic filaments would not fracture under a while range of applied stresses and thus, fragments of the cosmetic filaments are less likely to fall into the eye and cause irritation.

Mechanical force may be applied using an applicator such as, for example, a mascara brush. In a particularly desirable embodiment, the mascara brush may be used to brush the mascara formulation in a direction of the extension of the eyelashes. As the mascara brush is brushed across the length of the cosmetic filaments, a mechanical force may be applied to the cosmetic filaments. The mechanical force may be applied simultaneously while a portion of the crosslinkable polymers in a fluid or partially fluid state is drawn out beyond the terminal end of the keratin fiber. Alternatively, the mechanical force may be applied after the cross-linkable polymers form a solid filamentous extension on the keratin fiber.

All patents and patent publications referred to herein are hereby incorporated by reference.

Certain modifications and improvements will occur to those skilled in the art upon a reading of the foregoing description. It should be understood that all such modifications and improvements have been deleted herein for the sake of conciseness and readability but are properly within the scope of the following claims.

The invention claimed is:
1. A method for forming a filament on a keratin fiber comprising:
  (a) applying to said keratin fiber a composition comprising:
    (i) one or more cross-linkable polymers, wherein the one or more cross-linkable polymers comprise:
      (a) a siloxane polymer, wherein the siloxane polymer has the following structure:

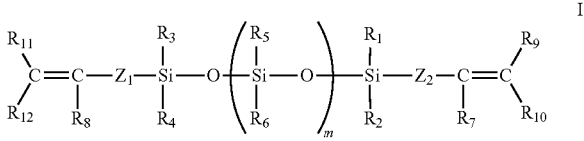

wherein,
m is an integer greater than 2;
$Z_1$ and $Z_2$ are independently selected from the group consisting of a bond between Si and the adjacent olefinic carbon atom, optionally substituted, branched or straight chain alkyl, alkenyl, alkynyl, aryl, heteroaryl, alkyl-aryl, alkoxy, O, S, and $NR^a$, wherein $R^a$ is selected from a group consisting of an alkyl, alkynyl, aryl, heteroaryl, and alkyl-aryl;
$R_1$, $R_2$, $R_3$, $R_4$, $R_5$, and $R_6$ are independently selected at each occurrence from the group consisting of branching points in the organopolysiloxane backbone whereby D, T, or Q structures are introduced, hydroxyl, hydrogen, carboxy, cyano, halogen, optionally substituted, branched, straight chain, or cyclic alkyl, alkenyl, alkynyl, aryl, alkyl-aryl, heteroalkyl, heteroaryl, alkoxy, amino, alkyl amino, and

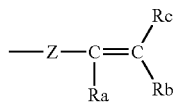

wherein Z is selected from the group consisting of a bond between Si and the adjacent olefinic carbon atom, optionally substituted, branched or straight chain alkyl, alkenyl, alkynyl, aryl, heteroaryl, alkyl-aryl, alkoxy, O, S, and $NR^a$, wherein $R^a$ is selected from a group consisting of an alkyl, alkynyl, aryl, heteroaryl, and alkyl-aryl, and wherein $R_a$, $R_b$, and $R_c$ are independently selected from hydrogen, hydroxyl, carboxy, cyano, halogen, optionally substituted branched or straight chain alkyl, alkenyl, alkynyl, aryl, heteroaryl, alkoxy, amino, or alkyl amino;

$R_7$ and $R_8$ are independently selected from the group consisting of hydrogen and unsubstituted branched or straight chain alkyl, alkenyl, and alkynyl; and $R_9$, $R_{10}$, $R_{11}$ and $R_{12}$ are independently selected the group consisting of hydrogen, hydroxyl, hydrido, carboxy, cyano, halogen, optionally substituted branched, straight chain or cyclic alkyl, alkenyl, alkynyl, heteroalkyl, aryl and heteroaryl, alkyl-aryl, alkoxy, amino, and alkyl amino, and (b) a hydrosilane, wherein the hydrosilane has the following structure:

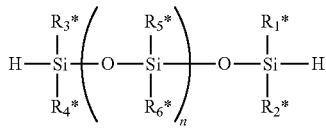

wherein $R_1^*$, $R_2^*$, $R_3^*$, $R_4^*$, $R_5^*$, and $R_6^*$ are independently selected at each occurrence from the group consisting of branching points in the organopolysiloxane backbone whereby D, T, or Q structures are introduced, alkyl, alkenyl, alkynyl, aryl heteroaryl, alkoxy, amino, alkyl amino, dialkyl amino, hydroxyl, hydrido, carboxy, cyano, halogen, and

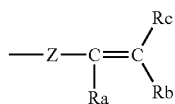

wherein Z is selected from the group consisting of a bond between Si and the adjacent olefinic carbon atom, optionally substituted, branched or straight chain alkyl, alkenyl, alkynyl, aryl, heteroaryl, alkyl-aryl, alkoxy, O, S, and $NR^a$, wherein $R^a$ is selected from a group consisting of an alkyl, alkynyl, aryl, heteroaryl, and alkyl-aryl, and wherein $R_a$, $R_b$, and $R_c$ are independently selected from hydrogen, hydroxyl, carboxy, cyano, halogen, optionally substituted branched or straight chain alkyl, alkenyl, alkynyl, aryl, heteroaryl, alkoxy, amino, or alkyl amino, and (ii) a cross-linking agent, wherein said crosslinking agent is a catalyst selected from the group consisting of palladium, rhodium, and platinum;

(b) drawing out a portion of said polymers beyond a terminal end of said keratin fiber while the polymers are in a fluid or partially fluid state;

(c) permitting said polymers to cure to a solid, thereby forming a filamentous extension on said keratin fiber, and wherein said composition is free of colorants.

2. A method for forming a filament on a keratin fiber comprising:

(a) applying to said keratin fiber a composition comprising:
(i) one or more cross-linkable siloxane polymers, wherein the cross-linkable siloxane polymer has the following structure:

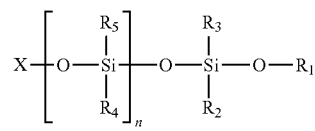

wherein, n is an integer greater than 3;

$R_1$ comprises a branched or straight chain $C_1$-$C_{10}$ alkyl group;

$R_2$ and $R_3$ are independently selected from the group consisting of amino, hydroxyl, hydrido, carboxy, cyano, halogen, optionally substituted branched or straight chain alkyl, alkenyl, alkynyl, alkoxy, aryl, and heteroaryl;

$R_4$ and $R_5$ are independently selected at each occurrence from the group consisting of amino, hydroxyl, hydrido, carboxy, cyano, halogen, optionally substituted branched or straight chain alkyl, alkenyl, alkynyl, aryl, heteroaryl, and alkoxy; and X comprises a chain terminating group, and ii) a cross-linking agent, wherein the cross-linking agent is a catalyst selected from the group consisting of tin, titanium and zirconium;

(b) drawing out a portion of said polymers beyond a terminal end of said keratin fiber while the polymers are in a fluid or partially fluid state; and (c) permitting said polymers to cure to a solid, thereby forming a filamentous extension on said keratin fiber, and wherein said composition is free of colorants.

3. The method of claim 2 wherein said cross-linking catalyst is an organo-tin complex, organotitanate or organozirconate.

4. The method of claim 1 or 2, wherein said keratin fiber is an eyelash and said filament on a keratin fiber extends beyond the terminal end of said keratin fiber by at least 1 mm.

5. The method of claim 1 or 2, wherein said keratin fiber is an eyelash and said filament on a keratin fiber extends beyond the terminal end of said eyelash by at least 5 mm.

6. The method of claim 1 or 2, further comprising irreversibly deforming said filament on a keratin fiber through application of a mechanical force to impart an arched shape.

* * * * *